United States Patent
Nadin et al.

(10) Patent No.: US 6,753,410 B2
(45) Date of Patent: Jun. 22, 2004

(54) INVESTIGATIONAL COMPOUNDS

(75) Inventors: Alan John Nadin, Swabridgeworth (GB); Joseph George Neduvelil, London (GB); Mohinder K. Sardana, Lansdale, PA (US); Jules A. Shafer, Gwynedd Valley, PA (US); Stephen J. Gardell, Blue Bell, PA (US); Ming-Tain Lai, Lansdale, PA (US); Yueming Li, Lansdale, PA (US); Bruce D. Dorsey, Ambler, PA (US); Dennis C. Dean, Chatham, NJ (US)

(73) Assignee: Merck & Co., Inc., Rahway, NJ (US)

( * ) Notice: Subject to any disclaimer, the term of this patent is extended or adjusted under 35 U.S.C. 154(b) by 152 days.

(21) Appl. No.: 09/797,820

(22) Filed: Mar. 2, 2001

(65) Prior Publication Data

US 2002/0013276 A1 Jan. 31, 2002

Related U.S. Application Data

(60) Provisional application No. 60/186,578, filed on Mar. 2, 2000.

(51) Int. Cl.⁷ .................................................. C07K 5/08
(52) U.S. Cl. .................... 530/331; 530/330; 514/17; 514/18; 548/303.7; 548/304.1; 435/7.5
(58) Field of Search ................................ 530/331, 330; 514/17, 18; 548/303.7, 304.1; 435/7.5

(56) References Cited

U.S. PATENT DOCUMENTS 5,703,129 A   12/1997   Felsenstein et al.   ........   514/613

FOREIGN PATENT DOCUMENTS

| EP | 0337714 | 4/1989 |
|---|---|---|
| EP | 0356223 | 8/1989 |
| EP | 0778266 | 6/1997 |
| WO | WO 98/15828 | 4/1998 |

OTHER PUBLICATIONS

Konvalinka et al, *Eur. J. Biochem.*, vol. 250, pp. 559–566 (1997).

Shearman, et al, *Biochemistry*, vol. 39, No. 30, pp. 8698–8704 (Jul. 6, 2000).

Price and Sisodia, *Annu. Rev. Neurosci.*, 21:479–505 (1998).

Selkoe, *J. Biol. Chem.*, 271(31), 18295–18298 (1996).

Steiner et al, *J. Biol. Chem.*, 274(12), 7615–7618 (1999).

Gosh, et al, *J. Org. Chem.*, 58, 1025–1029 (1993).

Hofmann, et al, *J. Am. Chem. Soc.*, 100:11, 3585–3590 (1978).

*Primary Examiner*—Christopher S. F. Low
*Assistant Examiner*—David Lukton
(74) *Attorney, Agent, or Firm*—John C. Todaro; Melvin Winokur

(57) ABSTRACT

The present invention is directed to compounds and pharmaceutical compositions comprising the compounds which are inhibitors of the enzyme gamma secretase and which are useful in the treatment or prevention of diseases in which the beta-amyloid peptide is involved, such as Alzheimer's disease.

5 Claims, No Drawings

INVESTIGATIONAL COMPOUNDS

This application claims benefit under 35 U.S.C. § 119(e) of U.S. Provisional application Ser. No. 60/186,538, filed Mar. 2, 2000.

The present invention relates to compounds, their salts, processes for making them and their use in investigating the processing of amyloid protein precursor and by extension Alzheimer's Disease.

Alzheimer's Disease (AD) is characterised by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The ragged $NH_2$- and COOH-termini of the native Aβ amyloid indicates that a complex mechanism of proteolysis is involved in its biogenesis.

The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-APP, and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

The present compounds are useful for investigating amyloidosis in particular in aiding the isolation and characterization of proteases involved in processing APP, especially where those proteases are γ-secretase and/or presenilin-1.

Accordingly, the present invention provides a compound of formula I or a salt thereof:

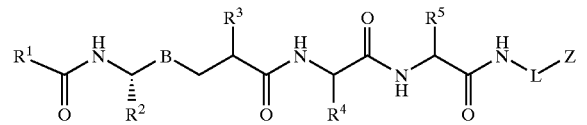

(I)

wherein:

$R^1$ is benzoylphenyl or benzoylphenyl$C_{1-6}$alkyl wherein the benzoylphenyl moiety is optionally substituted by from one to nine bromine atoms and the alkyl moiety is optionally substituted by $C_{1-6}$alkylsulfonylamino; or $C_{1-6}$alkoxy;

$R^2$ and $R^3$ are independently chosen from $C_{1-10}$alkyl, $C_{1-10}$alkoxy, $C_{2-10}$alkenyl, $C_2$ ioalkenyloxy, $C_{2-10}$alkynyl or $C_{2-10}$alkynyloxy; phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl, naphthyl, a five-membered heteroaromatic ring containing 1, 2, 3 or 4 heteroatoms independently chosen from O, N and S, at most one of the heteroatoms being O or S, and a six-membered heteroaromatic ring containing 1, 2 or 3 nitrogen atoms; and wherein each of $R^2$ and $R^3$ is independently optionally substituted by one to three groups independently chosen from:
(a) halogen, cyano and nitro,
(b) hydroxy,
(c) $C_{1-3}$alkyl, $C_{2-3}$ alkenyl and $C_{2-3}$alkynyl,
(d) $C_{1-3}$alkoxy,
(e) $NR^6R^7$ wherein $R^6$ and $R^7$ are independently chosen from hydrogen, $C_{1-5}$alkyl and $C_{1-5}$alkoxy$C_{1-5}$alkyl,
(f) $CO_2R^8$ wherein $R^8$ is hydrogen or $C^{1-4}$alkyl,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ is independently as defined above and $R^{8'}$ is independently as defined for $R^8$,
(k) $NR^8SO_2R^{8'}$ where $R^8$ and $R^{8'}$ are independently as defined above;

alternatively $R^3$ may be hydrogen;

$R^4$ and $R^5$ are independently chosen from hydrogen, $C_{1-6}$alkyl optionally substituted by halogen, hydroxy, thiol, amino, $C_{1-4}$alkoxy, $C_{1-4}$ alkylthio, carboxy, $C_{1-4}$ alkoxycarbonyl and $(CH_2)_qQ^2$ wherein $Q^2$ is a five-membered unsaturated heterocycle containing 1, 2, 3 or 4 heteroatom optionally chosen from O, N, and S providing that not more than one heteroatom is O or S, a six-membered unsaturated heterocycle containing 1, 2 or 3 N atoms and phenyl and naphthyl, or a fused ring which is indolyl, each of the foregoing rings being optionally substituted with one to three groups independently chosen from hydroxy, $C_{1-4}$alkyl, $C_{1-4}$alkoxy, thiol, $C_{1-4}$alkylthio, halogen, amino, carboxy, amido, $CO_2H$ and $—NHC(NH_2)_2$ and wherein each of the foregoing rings is optionally fused to a benzene ring;

alternatively $R^5$ may be benzoylbenzyl which is optionally substituted by from one to nine bromine atoms;

B is C=O or CHOH in the R configuration;

L is a bond or $[(CH_2)_mNHCO]_n$ in which one of the methylene groups may be replaced by a disulphide group;

Z is $(CH_2)_k$amino, benzoxy or biotin, or when L is a bond then Z is hydrogen or biotin providing that when Z is hydrogen then either $R^1$ is not $C_{1-6}$alkoxy or $R^5$ is benzoylbenzyl;

k is an integer of from one to ten;

each m is independently an integer of from one to ten;

n is an integer of from one to ten;

p is zero, one, two or three; and q is zero, one, two or three;
with the proviso that no carbon atom is substituted by more than one hydroxy group.

In an embodiment the compounds of the present invention are of formula I':

$$R^1 \underset{O}{\overset{}{\text{—C—}}} N(H) \underset{R^2}{\overset{OH}{\text{—CH—}}} CH_2 \underset{R^3}{\overset{}{\text{—CH—}}} C(O) N(H) \underset{R^4}{\overset{}{\text{—CH—}}} C(O) N(H) \underset{R^5}{\overset{}{\text{—CH—}}} C(O) N(H)\text{—L—}Z \quad (I')$$

where $R^1$, $R^2$, $R^3$, $R^4$, $R^5$, L and Z are as defined above.

In one embodiment the compounds of the present invention are of formula I":

$$(I'')$$

where $R^1$, $R^2$, $R^3$, $R^4$, $R^5$, L and Z are as defined above.

In another embodiment there are provided compounds of formula I''':

$$(I''')$$

where $R^1$, $R^2$, $R^3$, $R^4$, $R^5$, L and Z are as defined above.

The following preferred definitions of substituents apply to each of the formulae: I, I', I" and I''' which refer to those substituents.

Preferably $R^1$ is tertiarybutoxy or benzoylphenyl or benzoylphenyl$C_{1-2}$alkyl wherein the benzoylphenyl moiety is optionally substituted by from one to six, preferably by from one to four, bromine atoms, and the $C_{1-2}$alkyl moiety is optionally substituted by methylsulfonylamino.

Particular values of $R^1$ are tertiarybutoxy, benzoylphenyl, 2,3,5,6-tetrabromobenzoylphenyl, benzoylphenylethyl, (1-methylsulfonylamino)benzoylphenylethyl, benzoylphenylmethyl and 4-bromobenzoylphenyl.

$R^2$ and $R^3$ may be independently chosen from phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl; naphthyl; a five-membered heteroaromatic ring containing 1, 2, 3 or 4 heteroatoms independently chosen from O, N and S, at most one of the heteroatoms being O or S; and a six-membered heteroaromatic ring containing 1, 2 or 3 nitrogen atoms; and wherein each of $R^2$ and $R^3$ is independently optionally substituted by one to three groups independently chosen from:

(a) halogen, cyano and nitro,
(b) hydroxy,
(c) $C_{1-3}$alkyl, $C_{2-3}$alkenyl and $C_{2-3}$alkynyl,
(d) $C_{1-3}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above,
(k) $NR^8SO_2R^{8'}$ where $R^8$ and $R^{8'}$ are independently as defined above;

More preferably $R^2$ and $R^3$ are $(CH_2)_pQ^1$.

Preferably $Q^1$ is phenyl optionally substituted by one or two groups independently chosen from:

(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy and
(e) amino.

In one embodiment $R^2$ and $R^3$ are both benzyl.
More preferably $Q^1$ is phenyl.
$R^2$ and $R^3$ are especially benzyl.

Preferably $R^4$ and $R^5$ are independently chosen from optionally substituted $C_{1-6}$alkyl and $(CH_2)_qQ^2$. More preferably $R^4$ and $R^5$ are independently chosen from $C_{1-6}$alkyl and $(CH_2)_qQ^2$.

Preferably $Q^2$ is optionally substituted phenyl. More preferably $Q^2$ is phenyl.

In particular $R^4$ and $R^5$ are independently chosen from methyl, benzyl, phenyl, 2-methylpropyl, 1-hydroxyethyl and isobutyl. $R^4$ is particularly isobutyl.

$R^5$ is optionally benzoylbenzyl optionally substituted by from one to six bromine atoms, particularly by from one to four bromine atoms. $R^5$ may be unsubstituted benzoylbenzyl or benzyl.

L is preferably $[(CH_2)_mNHCO]_n$. Particular values of L-Z are biotincarbonylamino"pentyl, amino, biotincarbonylamino"pentylcarbonylamino"pentyl, botincarbonylamino"-pentylcarbonylamino"pentylcarbonylamino"pentyl, biotincarbonylamino"pentylcarbonylamino"pentylcarbonylamino"pentylearbon ylamino"pentyl, blotincarbonylaminoethyldlsulphidethylcarbonylamino"pentylcarbonylamino"pentylcarbonylamino"pentylcarbonylamino"-pentyl, benzoxycarbonylamino"pentylcarbonylamino"pentyl, benzoxycarbonylamino"pentylcarbonylamino"pentylcarbonylamino"pentylcarb onylamino"pentyl and amino"-butylcarbonylamino"pentylcarbonylamino"pentylcarbonylamino"pentyl.

Z is preferably biotin.
k is preferably an integer from three to five, such as four.
m is preferably an integer of from two to seven, more preferably from three to six, especially five.
n is preferably an integer of from one to seven, particularly from one to five.
p is preferably one.
q is preferably zero or one.

Thus a subclass of compounds is provided wherein:
$R^1$ is tertiarybutoxy, benzoylphenyl or benzoylphenyl$C_{1-2}$alkyl wherein the benzoylphenyl moiety is optionally substituted by from one to four bromine atoms and the $C_{1-2}$alkyl moiety is optionally substituted by methylsulfonylamino;

R² and R³ are benzyl;
R⁴ is isobutyl;
R⁵ is benzyl or benzoylbenzyl;
B is CHOH in the R configuration;
L is a bond or $[(CH_2)_m NHCO]_n$ in which one of the methylene groups may be replaced by a disulphide group;
Z is $(CH2)_k$amino, benzoxy or biotin, or when L is a bond then Z is hydrogen providing either R¹ is not tertiary butoxy or R⁵ is not benzyl;
k is four;
m is five; and
n is an integer of from one to five.

For the avoidance of doubt each time the moieties R⁶, R⁷, R⁸ and R⁸' occur they are chosen independently.

Also for the avoidance of doubt, radiolabelled compounds are encompassed within the above formulae. Thus, for example, hydrogen atoms may be replaced by tritium atoms.

For the avoidance of doubt "biotin" in the above definitions means the residue left when $CO_2H$ is removed from commercially available biotin.

As used herein, the expression "$C_{1-10}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-6}$alkyl", "$C_{1-4}$alkyl", "$C_{2-10}$alkenyl", "$C_{2-4}$alkenyl", "$C_{2-10}$alkynyl and "$C_{2-4}$alkynyl" are to be construed in an analogous manner.

The expression "$C_{3-7}$cycloalkyl" as used herein includes cyclic propyl, butyl, pentyl, hexyl and heptyl groups such as cyclopropyl and cyclohexyl.

The term "heterocyclic" includes rings which are saturated, partially saturated or unsaturated. Unsaturated heterocyclic rings are also known as beteroaromatic rings.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine. Suitable saturated heterocyclic rings include piperazine, morpholine, piperidine, tetrahydrofuran and tetrahydrothiophene. Tetrahydrofuran is preferred.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy and butoxy groups, including cyclopropylmethoxy.

Specific Examples according to the present invention include:

{4R-[1S-(2-(4-benzoyl-phenyl)-1-{5-[5-(2-oxo-(3aR,6aS)hexahydro-thieno[3,4-d]imidazol-6S-yl)-pentanoylamino]-pentylcarbamoyl}-ethylcarbamoyl)-3-(1S)-methyl-butylcarbamoyl]-1S-benzyl-2R-hydroxy-5-phenyl-pentyl}-carbamic acid tert-butyl ester;

4-benzoyl-N-{4R-[1S-(2-(4-benzoyl-phenyl)-1-{5-[5-(2-oxo-(3aR,6aS)hexahydro-thieno[3,4-d]imidazol-6S-yl)-pentanoylamino]-pentylcarbamoyl}-ethylcarbamoyl)-3(1S)-methyl-butylcarbamoyl]-1S-benzyl-2R-hydroxy-5-phenyl-pentyl}-benzamide;

(4R-{1S-[2-(4-benzoyl-phenyl)-1-carbamoyl-ethylcarbamoyl]-3(1S)-methyl-butylcarbamoyl}-1S-benzyl-2R-hydroxy-5-phenyl-pentyl)-carbamic acid tert-butyl ester;

4-benzoyl-N-{1S-benzyl-4R-[1-(1-carbamoyl-2S-phenyl-ethylcarbamoyl)-3(1S)-methyl-butylcarbamoyl]-2R-hydroxy-5-phenyl-pentyl}-benzamide;

4-benzoyl-N-{1S-benzyl-4R-[-(1-carbamoyl-2S-phenyl-ethylcarbamoyl)-3(1S)-methyl-butylcarbamoyl]-2R-hydroxy-5-phenyl-pentyl}-2,3,5,6-tetrabromo-benzamide;

5S-[3-(4-benzoyl-phenyl)-propionylamino]-2R-benzyl-4R-hydroxy-6-phenyl-hexanoic acid [1-(1-carbamoyl-2S-phenyl-ethylcarbamoyl)-3(1S)-methyl-butyl]-amide;

5S-[3-(4-benzoyl-phenyl)-2S-methanesulfonylamino-propionylamino]-2R-benzyl-4R-hydroxy-6-phenyl-hexanoic acid [1-(1-carbamoyl-2S-phenyl-ethylcarbamoyl)-3(1S)-methyl-butyl]-amide;

N-{1S-benzyl-4R-[1-(1-carbamoyl-2S-phenyl-ethylcarbamoyl)-3(1S)-methyl-butylcarbamoyl]-2R-hydroxy-5-phenyl-pentyl}-4-(4-bromo-benzoyl)-benzamide;

4-benzoyl-N-{1S-benzyl-2R-hydroxy-4R-[3-methyl-1S-(1-{5-[5-(2-oxo-(3aR,6aS)hexahydro-thieno[3,4-d]imidazol-6S-yl)-pentanoylamino]-pentylcarbamoyl}-2S-phenyl-ethylcarbamoyl)-butylcarbamoyl]-5-phenyl-pentyl}-benzamide;

{1S-benzyl-2R-hydroxy-4R-[3(1S)-methyl-1-(1-{5-[5-(2-oxo-(3aR,6aS)hexahydro-thieno[3,4-d]imidazol-6S-yl)-pentanoylamino]-pentylcarbamoyl}-2S-phenyl-ethylcarbamoyl)-butylcarbamoyl]-5-phenyl-pentyl}-carbamic acid tert-butyl ester;

(1S-benzyl-2R-hydroxy-4R-{3(1S)-methyl-1-[1-(5-{6-[5-(2-oxo(3aR,6aS)-hexahydro-thieno[3,4-d]imidazol-6S-yl)-pentanoylamino]-hexanoylamino}-pentylcarbamoyl)-2S-phenyl-ethylcarbamoyl]-butylcarbamoyl}-5-phenyl-pentyl)-carbamic acid tert-bytyl ester;

[1S-benzyl-2R-hydroxy-4R-(3(1S)-methyl-1-{1-[5-(6-{6-[5-(2-oxo(3aR,6aS)-hexahydro-thieno[3,4-d]imidazol-6S-yl)-pentanoylamino]-hexanoylamino}-hexanoylamino)-pentylcarbamoyl]-2S-phenyl-ethylcarbamoyl}-butylcarbamoyl)-5-phenyl-pentyl]-carbamic acid tert-butyl ester;

[1S-benzyl-2R-hydroxy-4R-(3(1S)-methyl-1-{1-[5-(6-(6-{6-[5-(2-oxo(3aR,6aS)-hexahydro-thieno[3,4-d]imidazol-6S-yl)-pentanoylamino]-hexanoylamino}-hexanoylamino)-hexanoylamino)-pentylcarbamoyl]-2S-phenyl-ethylcarbamoyl}-butylcarbamoyl)-5-phenyl-pentyl]-carbamic acid tert-butyl ester;

[1S-benzyl-4R-(1-{1-[5-(6-benzyloxycarbonylamino-hexanoylamino)-pentylcarbamoyl]-2S-phenyl-ethylcarbamoyl}-3(1S)-methyl-butylcarbamoyl)-2R-hydroxy-5-phenyl-pentyl]-carbamic acid tert-butyl ester;

(1S-benzyl-4R-{1-[1-(5-{6-[6-(6-benzyloxycarbonyl-amino-hexanoylamino)-hexanoylamino]-hexanoylamino}-pentylcarbamoyl)-2S-phenyl-ethylcarbamoyl]-3(1S)-methyl-butylcarbamoyl}-2R-hydroxy-5-phenyl-pentyl)-carbamicacid tert-butyl ester;

(4R-{1S-[1-(5-{6-[6-(6-amino-hexanoylamino)-hexanoylamino]-hexanoylamino}-pentylcarbamoyl)-2-phenyl-ethylcarbamoyl]-3(1S)-methyl-butylcarbamoyl}-1S-benzyl-2R-hydroxy-5-phenyl-pentyl)-carbamic acid tert-butyl ester and (1S,2R,4R,7S,10S)-[52-(hexahydro-2-oxo-1H-thieno[3,4-d]imidazol-4-yl)-2-hydroxy-7-(2-methylpropyl)-5,8,11,19,26,33,40,48-octaoxo-1,4,10-tris(phenylmethyl)-43,44-dithia-6,9,12,18,25,32,39,47-octaazadopentacont-1-yl]carbamic acid 1,1-dimethylester The compounds of the present invention have an activity as inhibitors of γ secretase. In a preferred embodiment the compounds of the invention inhibit proteolysis of PS-1. The compounds can photoaffinity label the PS-1 beterodimer.

The present invention also provides a compound of the invention or a salt thereof for use in a method of investigating APP processing in amyloidosis.

There is also provided a process for producing a compound of formula I or a pharmaceutically acceptable salt thereof which comprises reacting a compound of formula II with a compound of formula III:

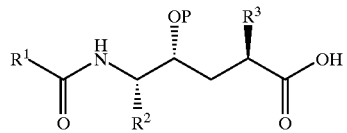

(II)

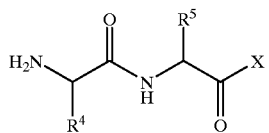

(III)

wherein $R^1$, $R^2$, $R^3$, $R^4$ and $R^5$ are as defined above, X is OH, $C_{1-6}$alkoxy or NHLZ where L and Z are as defined above and P is hydrogen or a protecting group such as a trialkylsilane group, for example t-butyl dimethylsilyl, followed, if necessary, by deprotection of the resulting compound and, if necessary by converting X into a group NHLZ. The reaction is generally carried out in the presence of coupling agents such as 1-(3-dimethylaminopropyl)-3-ethylcarbodiimide hydrochloride and 1-hydroxybenzotriazole, generally both at 1.2 equivalents, in a solvent such as DMF, generally at about room temperature for six to twelve hours. Any necessary deprotection is achieved by conventional means. Conversion of X into a group $NH_2$ can be achieved by, for example, reacting with N-methylmorpholine and isobutylchloroformate, both generally at 1 equivalent, followed by the addition of ammonia gas.

The compound of formula II is produced by reacting a compound of formula IV:

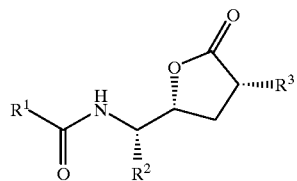

(IV)

wherein $R^1$, $R^2$ and $R^3$ are as defined above in a solvent such as dioxane, with a base such as lithium hydroxide in a polar solvent such as water generally at room temperature for above five hours. If desired the resulting compound of formula II in which P is hydrogen is protected by conventional means.

The compound of formula IV is produced by reacting a compound of formula V with a compound of formula VI or a compound of formula VII:

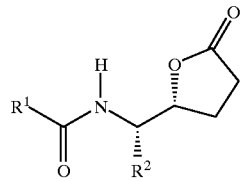

(V)

(VI)

(VII)

wherein $R^1$, $R^2$ and X are as defined above, $R^{3''}$ is the acyl derivative of a group $R^3$ as defined above and $R^{3'''}$ is a group $R^3$ bound to an oxo group at the portion of $R^3$ which connects to the compound of formula V. The reaction is generally carried out in the presence of a base such as lithium diisopropylamide in a solvent such as THF generally cooled to −78° C. for about thirty minutes. The reaction mixture is subsequently dehydrated without purification and then hydrogenated with, for example, hydrogen over 5% Pd/C catalyst at about 50 psi for about 2 h.

The compound of formula V in which $R^1$ is tertiary butyl and $R^2$ is benzyl can be prepared as described by J. Litera et al., Collect. Czech. Chem. Commun. 1998, 63, 231ff. Compounds of formula V in which $R^1$ is other than tertiary butyl and $R^2$ is other than benzyl can be made by analogous methods.

Compounds of formula III in which X is $C_{1-6}$alkoxy can be made by reacting a compound of formula XIII with a compound of formula VIII:

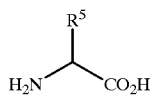

(XIII)

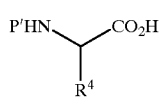

(VIII)

wherein $R^4$ and $R^5$ are as defined above and P' is a protecting group such as BOC, generally under the same conditions as for the reaction between compounds of formulae II and III. The compound of formula XIII is generally pre-reacted with HCl in $C_{1-6}$alcohol to produce the $C_{1-6}$alkyl ester hydrochloride salt. Compounds of formula III in which X is $NH_2$ can be made using the reaction at the end of the description for making compounds of formula I.

Compounds of formula III in which X is L—Z where L is not a bond and Z is as defined above can be made by reacting a compound of formula III in which X is OH and the free amine group is optionally protected, with a compound of formula IX:

$$H_2NLZ \quad (IX)$$

in which L is not a bond and Z is as defined above, generally under the same conditions as for the reaction between compounds of formulae II and III.

Compounds of formula IX can be made by reacting a compound of formula X with a compound of formula XI:

$$H_2NL'W \quad (X)$$

$$SuOCOL''Z \quad (XI)$$

where L' is $[(CH_2)_m\text{'NHCO}]_n\text{'}$, L" is $[(CH_2)_m\text{"NHCO}]_{n-n}\text{'}$ in which one of the methylene groups may be replaced by a disulphide group, m' and n' are as defined above, each m" is an integer from 1 to 10, n' is an integer from 1 to 9, W is $C_{1-6}$alkoxy, Z is as defined above and SuO is succinimidoxy optionally substituted at the 3-position with a group $NaSO_3$, generally with 1 equivalent of each and in the presence of a strong base such as triethylamine. The product obtained is deprotected, for example with TFA.

It will be understood that any compound of formula I initially obtained from the above process may, where appropriate, subsequently be elaborated into a further compound of formula I by techniques known from the art. For example, the nature of $R^1$ can be altered by reacting a compound of formula I in which the hydroxy group is protected, for example by a trialkylsilane group, and from which the RIO group has been removed, for example with TFA, with an appropriate acid or acid chloride generally under the same conditions as the reaction between compounds of formulae II and III.

The nature of $R^1$ in compounds of formula IV can be altered by analogous methods.

As a further example the L in L—Z of a compound of formula I can be lengthened where Z is benzoxy by hydrogenating, for example with 10% Pd/C under $H_2$ at pressure and in ethanol, and coupling the resulting amine with a compound of formula XII or XIV:

$$HOCOL'''Z \quad (XII)$$

$$SuOCOL'''Z \quad (XIV)$$

where L''' is $[(CH_2)_m\text{'''NHCO}]_n\text{'''}$ where m''' and n''' are as defined above for m and n but are no greater than nine and one of the methylene groups maybe replaced by a disulphide group and SuO and Z are as defined above, generally under the same conditions used for reacting the compounds of formulae II and III.

L in compounds of formula III can be lengthened by analogous methods.

Compounds of formulae VI, VII, VIII, X, XI, XII, XIII and XIV are commercially available or known in the prior art or can be made from commercially available or known compounds by standard methods.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.

(2) Cells are placed in 96-well plates at 30,000/well/100 μL in minimal essential medium (MEM) (phenol red-free)+10% foetal bovine serum (FBS), 50 mM HEPES buffer (pH7.3), 1% glutamine, 0.2mg/mL G418 antibiotic, 10 mM sodium butyrate.

(3) Make dilutions of the compound plate. Dilute stock solution to 5.5% DMSO/110 μM compound. Mix compounds vigorously and store at 4° C. until use.

(4) Add 10 μL compound/well. Mix plate briefly, and leave for 18 h in 37° C. incubator.

(5) Remove 90 μL of culture supernatant and dilute 1:1 with ice-cold 25 mM HEPES (pH.3), 0.1% BSA, 1.0 mM EDTA (+broad spectrum protease inhibitor cocktail; pre-aliquotted into a 96-well plate). Mix and keep on ice or freeze at −80° C.

(6) Add back 100 μL of warm MEM+10% FBS, 50 mM HEPES (pH7.3), 1% glutamine, 0.2 mg/mL G418, 10 mM sodium butyrate to each well, and return plate to 37° C. incubator.

(7) Prepare reagents necessary to determine amyloid peptide levels, for example by ELISA assay (8) To determine if compounds are cytotoxic cell viability following compound administration is assessed by the use of redox dye reduction. A typical example is a combination of redox dye MTS (Promega) and the electron coupling reagent PES. This mixture is made up according to the manufacturer's instructions and left at room temperature.

(9) Quantitate amyloid beta 40 and 42 peptides using an appropriate volume of diluted culture medium by standard ELISA techniques.

(10) Add 15 μL/well MTS/PES solution to the cells; mix and leave at 37° C.

(11) Read plate when the absorbance values are approximately 1.0 (mix briefly before reading to disperse the reduced formazan product).

The Examples of the present invention all had an $ED_{50}$ of less than 500 nM, preferably less than 200 nM and most preferably less than 100 nM in the above assay.

The following examples illustrate the present invention.

The following General Procedures were used throughout the Examples.

General Procedure A—Peptide Coupling

A solution of an amine component, an acid component, 1-[3-(dimethylamino)propyl]-3-ethylcarbodiimide hydrochloride (1.2 equivalents) and 1-hydroxybenzotriazole (1.2 equivalents) in DMF was stirred at room temperature overnight. If the amine component was present as a salt, one equivalent of triethylamine was added. The reaction mixture was diluted with ethyl acetate and washed with an aqueous solution of citric acid (10%) (twice), aqueous NaHCO$_3$ solution (twice) and brine. The organic phase was dried (MgSO$_4$), filtered and evaporated in vacuo. The crude product was either used without further purification, or purified by trituration, crystallization or flash column chromatography.

General Procedure B—Ester Hydrolysis

A solution of an ester in dioxane was treated with aqueous lithium hydroxide (3 equivalents, 1.0 M in H$_2$O) and stirred at room temperature. The reaction mixture was acidified with aqueous HCl and ethyl acetate. The organic layer was washed with brine, dried (MgSO$_4$), filtered and evaporated in vacuo. The crude product was either used directly without further purification, or purified by trituration or flash column chromatography.

General Procedure C—BOC Deprotection

A BOC-protected amine was dissolved in trifluoroacetic acid and stirred under nitrogen at room temperature. The reaction mixture was evaporated in vacuo and azeotroped with toluene (twice). The crude product was either used directly or purified by flash column chromatography.

General Procedure D—Silyl Ether Deprotection

A silyl ether was dissolved in an excess of a solution of TBAF in THF (1.0 M) and stirred at room temperature overnight. The reaction mixture was diluted with ethyl acetate and aqueous citric acid. The resulting precipitate was collected by filtration and washed with water and ether (several times). The crude product was either used directly without further purification, or purified by column chromatography. In cases where a precipitate was not formed, the reaction mixture was diluted with warm ethyl acetate and washed with dilute citric acid and brine. The organic phase was dried (MgSO$_4$), filtered and evaporated in vacuo. Purification by flash column chromatography gave the deprotected alcohol.

General Procedure E—Coupling an Amine and an N-hydroxysuccinimide Ester

An amine and an N-hydroxysuccinimide ester (1 equivalent) were dissolved in DMF and treated with triethylamine (1 equivalent) and stirred at room temperature for 1 h. The reaction mixture was diluted with ethyl acetate and washed with an aqueous solution of citric acid (10%) (twice), aqueous NaHCO$_3$ solution (twice) and brine. The organic phase was dried (MgSO$_4$), filtered and evaporated in vacuo. The crude product was either used without further purification, or purified by trituration or flash column chromatography.

EXAMPLE 1 (SCHEME 1)

{4R-[1S-(2-(4-Benzoyl-phenyl)-1-{5-[5-(2-oxo-(3aR,6aS)hexahydro-thieno [3,4-d]imidazol-6S-yl)-pentanoylamino]-pentylcarbamoyl}-ethylcarbamoyl)-3-(1S)-methyl-butylcarbamoyl]-1S-benzyl-2R-hydroxy-5-phenyl-pentyl}-carbamic acid tert-butyl ester.

Step 1: [1S-(4R-Benzyl-5-oxo-tetrahydrofuran-2R-yl)-2-phenylethyl]-carbamic acid, tert-butyl ester A solution of [1S-(5-oxo-tetrahydrofuran-2R-yl)-2-phenylethyl]-carbamic acid, tert-butyl ester (prepared as described in J. Litera et al., *Collect. Czech. Chem. Commun.* 1998, 63, 231) (3.0 g, 0.99 mmol) in THF (10 ml) was added to a solution of lithium diusopropylamide [made from n-butyllithium (8.64 ml of a 2.5 M solution in hexane) and diisopropylamine (3.06 ml)] in THF (10 ml) at −78° C. The reaction mixture was stirred for 40 minutes at −78° C., then treated with benzaldehyde. After 30 minutes, the reaction mixture was quenched by the addition of aqueous NH$_4$Cl (5 ml) and water. The resulting mixture was extracted with ethyl acetate and the combined extracts were washed with aqueous citric acid, aqueous NaHCO$_3$ solution and brine. The combined extracts were dried (MgSO4), filtered and evaporated in vacuo to give a thick oil. This crude reaction product was treated with acetic anhydride (5 ml), triethylamine (5 ml) and heated at 120° C. for 1 h. The reaction mixture was cooled to room temperature, diluted with ether and washed with aqueous citric acid, aqueous NaHCO$_3$ solution and brine. The ethereal extracts were dried (MgSO$_4$) and evaporated in vacuo to give the reaction product as a crude solid which was used without further purification. This crude reaction product was dissolved in ethyl acetate (25 ml) and methanol (5 ml), treated with 5% Pd/C catalyst and hydrogenated at 50 psi for 2 h. The reaction mixture was filtered and evaporated in vacuo to give the title compound, which was either purified by flash column chromatography, or by trituration with ether, (yield 3.9 g, 78%). $^1$H NMR (250 MHz, CDCl$_3$) 7.38–7.15 (10H, m); 4.38–4.11 (2H, m), 3.90 (1H, brs); 3.27 (1H, dd, J=13.7, 4.0); 2.95–2.67 (4H, m), 2.28–2.17 (1H, m); 1.86–1.70 (1H, m); 1.34 (9H, s)

Step 2: 2R-Benzyl-5S-tert-butoxycarbonylamino-4R-(tert-butyldimethylsilanyloxy)-6-phenyl-hexanoic acid The compound obtained in Step 1 (2.0 g, 5.1 mmol) was dissolved in 1,2-dimethoxyethane (36 mL) and treated with a solution of sodium hydroxide in water (1.0 M, 36 mL, 1.1 equiv.) and stirred at room temperature for 0.5 h. The reaction mixture was carefully acidified to pH 4 with citric acid, then extracted with ethyl acetate. The ethyl acetate extracts were washed with brine, dried (MgSO$_4$), filtered and evaporated in vacuo. The crude hydroxyacid was dissolved in DMF (20 mL) and treated with tert-butyldimethylsilyl chloride (7.8 g, 5 equiv.) and imidazole (4.2 g, 10 equiv.) and stirred overnight. The reaction mixture was treated with methanol and stirred for 2 h, then evaporated in vacuo. The reaction mixture was partitioned between aqueous citric acid and ethyl acetate. The organic layer was washed with brine, dried (MgSO$_4$), filtered and evaporated in vacuo. Purification by flash column chromatography gave the title compound (2.55 g, 95%) $^1$H NMR (400 MHz, d$_6$-DMSO) 12.08 (1H, s); 7.25–7.04 (10H, m); 6.45 (1H, d, J=8.9); 3.74–3.53 (2H, m); 2.76–2.50 (5H, m); 1.8–1.5 (2H, m); 1.22 (9H, s); 0.80 (9H, s); 0.07 (3H, s); 0.05 (3H, s).

Step 3

{4R-[1S-(2-(4-Benzoyl-phenyl)-1-{5-[5-(2-oxo-(3aR,6aS)hexahydro-thieno[3,4-d]imidazol-6S-yl)-pentanoylamino]-pentylcarbamoyl}-ethylcarbamoyl)-3-(1S)-methyl-butylcarbamoyl]-1S-benzyl-2R-hydroxy-5-phenyl-pentyl}-carbamic acid tert-butyl ester 4-Benzoylphenylalanine (0.3 g) was dissolved in 4N HCl/MeOH and stirred at room temperature overnight. The reaction mixture was evaporated in vacuo and triturated with ether to give the methyl ester hydrochloride salt. This was reacted with BOC-L-Leu-OH following General Procedure A to give dipeptide 1. This was hydrolyzed with LiOH following General Procedure B, and the product of this reaction was reacted with amine A (commercially available) following General Procedure A. The resulting product was deprotected with TFA following General Procedure C, and the resulting product was reacted with the product of Step 2 (B) following General Procedure A. The resulting product was treated with TBAF according to General Procedure D.

(1H, DMSO) 7.90–7.02 (24H, m), 6.45 (1H, d, J=9.0), 6.38 (1H, s), 6.34 (1H, s), 4.80–4.00 (5H, m), 3.50–2.45 (16H, m), 2.01 (apparent t, J=7.2, 2H), 1.67–0.75 (22H, m).

EXAMPLE 2 (SCHEME 1)

4-Benzoyl-N-{4R-[1S-(2-(4-benzoyl-phenyl)-1-{5-[5-(2-oxo-(3aR,6aS)hexahydro-thieno[3,4-d]imidazol-6S-yl)-pentanoylamino]-pentylcarbamoyl}-ethylcarbamoyl)-3(1S)-methyl-butylcarbamoyl]- 1S-benzyl-2R-hydroxy-5-phenyl-pentyl}-benzamide In the same way the above compound was made starting from 2R-benzyl-5S-parabenzoylphenylamino-4R-(tert-butyldimethylsilanyloxy)-6-phenyl-hexanoic acid (C) made by analogous methods to the product of Example 1 Step 2.

(1H, DMSO) 8.36 (1H, d, J=8.5), 7.99–6.92 (32H, m), 6.40 (1H, s), 6.34 (1H, s), 4.92 (1H, d, J=6.1), 4.51–4.49 (1H, m), 4.30–4.08 (4H, m), 3.60–3.54 (1H, m), 3.10–2.50 (12H, m), 2.01 (2H, apparent t, J=7.1), 1.8–1.1 (17H, m), 0.77 (3H, d, J=6.5), 0.72 (3H, d, J=6.5).

EXAMPLE 3 (SCHEME 1)

(4R-{1S-[2-(4-Benzoyl-phenyl)-1-carbamoyl-ethylcarbamoyl]-3(1S)-methyl-butylcarbamoyl}1S-benzyl-2R-hydroxy-5-phenyl-pentyl)-carbamic acid tert-butyl ester 4-Benzoylphenylalanine was dissolved in 4N HCl/MeOH and stirred at room temperature overnight. The reaction mixture was evaporated in vacuo and triturated with ether to give the methyl ester hydrochloride salt. This was reacted with BOC-L-Leu-OH following General Procedure A to give dipeptide 1. This was deprotected with TFA following General Procedure C, and coupled with the product of Example 1 Step 2 (B) following General Procedure A. The resulting product was hydrolyzed following General Procedure B. The resulting product (100 mg) was dissolved in THF and treated with N-methylmorpholine (1 equivalent), cooled to –18° C. and treated with isobutyl chloroformate (1 equivalent). The reaction mixture was stirred for 10 min. Ammonia was then bubbled into the reaction mixture for two minutes, which was then allowed to warm to room temperature. The reaction mixture was diluted with ethyl acetate and water. The organic layer was dried, filtered and evaporated. The resulting product was purified by flash column chromatography, then treated with TBAF following General Procedure D.

(1H, DMSO) 7.95–7.02 (23H, m), 6.51–6.48 (1H, m), 4.72–4.68 (1H, m), 4.51–4.46 (1H, m), 4.21–4.15 (1H, m), 3.50–2.40 (9H, m), 1.7–1.1 (14H, m), 0.9–0.7 (6H, m).

EXAMPLES 4–7 (SCHEME 2)

4-Benzoyl-N-{1S-benzyl-4R-[1-(1-carbamoyl-2S-phenyl-ethylcarbamoyl)-3(1S)-methyl-butylcarbamoyl]-2R-hydroxy-5-phenyl-pentyl}-benzamide 4-Benzoyl-N-{1S-benzyl-4R-[1-(1-carbamoyl-2S-phenyl-ethylcarbamoyl)-3(1S)-methyl-butylcarbamoyl]-2R-hydroxy-5-phenyl-pentyl}-2,3,5,6-tetrabromo-benzamide 5S-[3-(4-Benzoyl-phenyl)-propionylamino]-2R-benzyl-4R-hydroxy-6-phenyl-hexanoic acid [1-(1-carbamoyl-2S-phenyl-ethylcarbamoyl)-3(1S)-methyl-butyl]-amide 5S-[3-(4-Benzoyl-phenyl)-2S-methanesulfonylamino-propionylamino]-2R-benzyl-4R-hydroxy-6-phenyl-hexanoic acid [1-(1-carbamoyl-2S-phenyl-ethylcarbamoyl)-3(1S)-methyl-butyl]-amide The product of Example 1 Step 2 was treated with TFA for 5 minutes, then evaporated in vacuo and azeotroped with toluene twice. Purification by flash column chromatography gave the free amine. This was reacted with an acid according to General Procedure A, and the resulting product deprotected with TBAF following General Procedure D.

EXAMPLE 4

(1H, DMSO) 8.32 (1H, d, J=8), 7.90–7.52 (11H, m), 7.32–7.05 (17H, m), 4.92 (1H, d, J=6), 4.43–4.39 (1H, m), 4.19–4.02 (2H, m), 3.61–3.56 (1H, m), 3.02–2.52 (6H, m), 1.76–1.27 (6H, m), 0.78 (3H, d, J=6.5), 0.73 (3H, d, J=6.5).

EXAMPLE 5

(1H, DMSO) 8.64–8.62 (1H, m), 8.01–7.03 (24H, m), 4.75–4.62 (1H, m), 4.45–4.38 (1H, m), 4.25–4.10 (2H, m), 3.72–3.68 (1H, m), 3.50–2.50 (6H, m), 1.90–0.75 (12H, m).

EXAMPLE 6

(1H, DMSO) 7.87 (1H, d, J=7.6), 7.73–7.53 (8H, m), 7.29–7.04 (18H, m), 4.80 (1H, d, J=5.4), 4.44–4.38 (1H, m), 4.17–4.12 (1H, m), 3.90–3.75 (1H, m), 3.45–3.40 (1H, m), 3.00 (1H, dd, J=4.9, 5.1), 2.86–2.69 (6H, m), 2.57–2.26 (6H, m), 1.65–1.22 (5H, m), 0.81 (3H, d, J=6.4), 0.75 (3H, d, J=6.4).

EXAMPLE 7

(1H, DMSO) 8.04 (1H, d, J=9.2), 7.91 (1H, d, J=7.7), 7.72–7.66 (6H, m), 7.58–7.54 (2H, m), 7.39–7.07 (20H, m), 4.84 (1H, d, J=6.2), 4.42–4.39 (1H, m), 4.19–4.15 (1H, m), 3.95–3.92 (2H, m), 3.40–3.38 (1H, m), 3.00 (1H, dd, J=5.2, 13.8), 2.85–2.44 (8H, m), 2.13 (3H, s), 1.72–1.65 (1H, m), 1.58–1.30 (4H, m), 0.82 (3H, d, J=6.4), 0.75 (3H, d, J=6.4).

EXAMPLES 8 AND 9 (SCHEME 3)

N-{1S-Benzyl-4R-[1-(1-carbamoyl-2S-phenyl-ethylcarbamoyl)-3(1S)-methyl-butylcarbamoyl]-2R-hydroxy-5-phenyl-pentyl}-4-(4-bromo-benzoyl)-benzamide 4-Benzoyl-N-{1S-benzyl-2R-hydroxy-4R-[3-methyl- 1S-(1-{5-[5-(2-oxo-(3aR,6aS)hexahydro-thieno[3,4-d]imidazol-6S-yl)-pentanoylamino]-pentylcarbamoyl}-2S-phenyl-ethylcarbamoyl)-butylcarbamoyl]-5-phenyl-pentyl}-benzamide A solution of the product of Example 1 Step 1 was treated with TFA according to General Procedure C. The resulting product was coupled with an acid according to General Procedure A. The resulting products were ring-opened according to the procedure in J. Org. Chem., 1993, 1028. The resulting acids were coupled with H$_2$N-Leu-Phe-CONH$_2$ or H$_2$N-Leu-Phe-NH(CH$_2$)$_5$NH- Biotin according to General Procedure A and deprotected with TBAF following General Procedure D.

EXAMPLE 8

(1H, DMSO) 8.33 (1H, d, J=9.0), 7.90–7.64 (10H, m), 7.29–7.07 (17H, m), 4.93 (1H, d, J=6.0), 4.42–4.39 (1H, m), 4.18–4.05 (2H, m), 3.62–3.52 (1H, m), 3.02–2.56 (7H, m), 1.75–1.30 (5H, m), 0.78 (3H, d, J=6.4), 0.73 (3H, d, J=6.4).

EXAMPLE 9

(1H, DMSO) 8.34 (1H, d, J=9.0), 7.91–7.69 (11H, m), 7.60–7.57 (2H, m), 7.25–7.11 (16H, m), 6.41 (1H, s), 6.35

(1H, s), 4.94 (1H, d, J=6), 4.44–4.12 (5H, m), 3.62–3.58 (1H, m), 3.19–2.56 (13H, m), 2.03 (2H, apparent t, J=7), 1.73–0.9 (17H, m), 0.79 (3H, d, J=6.5), 0.74 (3H, d, J=6.5).

EXAMPLE 10 (SCHEME 3)

{1S-Benzyl-2R-hydroxy-4R-[3(1S)-methyl-1-(1-{5-[5-(2-oxo-(3aR,6aS)hexahydro-thieno[3,4-d]imidazol-6S-yl)-pentanoylamino]-pentylcarbamoyl}-2S-phenyl-ethylcarbamoyl)-butylcarbamoyl]-5-phenyl-pentyl}-carbamic acid tert-butyl ester The product of Example 1 Step 2 was coupled with H$_2$N-Leu-Phe-NH(CH$_2$)$_5$NH-Biotin according to General Procedure A and deprotected with TBAF following General Procedure D.

(1H, CDCl$_3$) 0.75 (3H, d, J=3.5 Hz), 0.84 (3H, d, J=3.5 Hz), 1.1–1.2 (2H, m), 1.23 (9H, s), 1.27–1.7 (16H, m), 2.05 (2H, t, J=3.0 Hz), 2.68–3.2 (12H, m), 3.16 (1H, s), 3.17 (1H, s), 3.49 (2H, m), 4.25 (2H, m), 4.29 (1H, m), 4.40 (1H, m), 4.7 (1H, d, J=2.5 Hz), 6.3 (1H, s), 6.4 (1H, s), 6.49 (1H, d, J=3.0 Hz), 7.0–7.28 (15H, m), 7.67 (1H, m), 7.75 (1H, m), 7.9 (1H, m)

EXAMPLE 11 (SCHEME 4)

(1S-Benzyl-2R-hydroxy-4R-{3(1S)-methyl-1-[1-(5-{6-[5-(2-oxo(3aR,6aS)-hexahydro-thieno[3,4-d]imidazol-6S-yl)-pentanoylamino]-hexanoylamino}-pentylcarbamoyl)-2S-phenyl-ethylcarbamoyl]-butylcarbamoyl}-5-phenyl-pentyl)-carbamic acid tert-butyl ester SuO-LC-Biotin (commercially available) was reacted with H$_2$N(CH$_2$)$_5$NHBOC following General Procedure E. The resulting product was deprotected according to General Procedure C and the resulting product coupled with BOC—Leu—Phe—OH following General Procedure A. This product was deprotected with TFA following General Procedure C. This product was coupled with the product of Example 1 Step 2 following General Procedure A, and the resulting product was deprotected with TBAF following General Procedure D.

(1H, DMSO) 7.89–7.66 (5H, m), 7.24–7.07 (16H, m), 6.47 (1H, d, J=8.9), 6.41 (1H, s), 6.35 (1H, s), 4.7 (1H, brs), 4.40 (1H, q, J=6.8), 4.30 (1H, dd, J=5.0, 5.0), 4.18–4.12 (2H, m), 3.5–2.5 (10H, m), 2.03 (2H, dd, J=7.2), 1.65–1.13 (41H, m), 0.82 (3H, d, J=6.4), 0.75 (3H, d, J=6.4).

EXAMPLE 12 (SCHEME 5)

[1S-Benzyl-2R-hydroxy-4R-(3(1S)-methyl-1-{1-[5-(6-{6-[5-(2-oxo(3aR,6aS)-hexahydro-thieno[3,4-d]imidazol-6S-yl)-pentanoylamino]-hexanoylamino}-hexanoylamino)-pentylcarbamoyl]-2S-phenyl-ethylcarbamoyl}-butylcarbamoyl)-5-phenyl-pentyl]-carbamic acid tert-butyl ester NH$_2$(CH$_2$)$_5$NH—LC—Z was reacted with BOC-Leu-Phe-OH following General Procedure A. The resulting product was deprotected following General Procedure C and coupled with the product of Example 1 Step 2 (B) following General Procedure A. The resulting product was deprotected with TBAF following General Procedure D.

(1H, DMSO) 7.90–7.61 (4H, m), 7.40–7.03 (21H, m), 6.48 (1H, d, J=8.2), 4.99 (2H, s), 4.70 (1H, d, J=7.3), 4.42–4.38 (1H, m), 4.19–4.15 (1H, m), 3.52–3.42 (2H, m), 3.05–2.45 (14H, m), 2.00 (apparent t, J=7.1, 2H), 1.70–1.08 (27H, m), 0.82 (3H, d, J=6.4), 0.75 (3H, d, J=6.4).

EXAMPLES 13 AND 14 (SCHEME 5)

[1S-Benzyl-2R-hydroxy-4R-(3(1S)-methyl-1-{1-[5-(6-(6-{6-[5-(2-oxo(3aR,6aS)-hexahydro-thieno[3,4-d]imidazol-6S-yl)-pentanoylamino]-hexanoylamino}-hexanoylamino)-hexanoylamino)-pentylcarbamoyl]-2S-phenyl-ethylcarbamoyl}-butylcarbamoyl)-5-phenyl-pentyl]-carbamic acid tert-butyl ester

[1S-Benzyl-4R-(1-{1-[5-(6-benzyloxycarbonylamino-hexanoylamino)-pentylcarbamoyl]-2S-phenyl-ethylcarbamoyl}-3(1S)-methyl-butylcarbamoyl)-2R-hydroxy-5-phenyl-pentyl]-carbamic acid tert-butyl ester NH$_2$(CH$_2$)$_5$NH—LC—Z (where Z is benzyloxycarbonyl) was reacted with BOC-Leu-Phe-OH following General Procedure A. The resulting product was deprotected following General Procedure C and coupled with the product of Example 1 Step 2 (B) following General Procedure A. The resulting product (110 mg) was dissolved in methanol (5 ml) and treated with Pd/C (5%) and hydrogenated at 50 psi for 1 h. The reaction mixture was filtered through Celite and evaporated in vacuo to give the amine (92 mg, 91%). This was coupled with SuO-LC-Biotin or SuO-LC—LC-Biotin following General Procedure E and the resulting products deprotected with TBAF following General Procedure D.

EXAMPLE 13

(1H, DMSO) 7.66 (1H, d, J=7.3), 7.53–7.42 (5H, m), 7.23–7.10 (15H, m), 6.14 (3H, m), 4.50–4.11 (5H, m), 3.50–3.45 (m, 2H), 3.06–2.55 (18H, m), 2.09–2.03 (6H, m), 1.67–1.15 (38H, m), 0.82 (3H, d, J=6.5), 0.77 (3H, d, J=6.5).

EXAMPLE 14

(1H, DMSO) 7.66 (1H, d, J=7.3), 7.53–7.42 (6H, m), 7.23–7.09 (15H, m), 6.15 (3H, m), 4.51–4.12 (5H, m), 3.49–3.47 (2H, m), 3.05–2.55 (22H, m), 2.07–2.00 (6H, m), 1.67–1.15 (44H, m), 0.82 (3H, d, J=6.5), 0.77 (3H, d, J=6.5).

EXAMPLE 15 (SCHEME 6)

(1S-Benzyl-4R-{1-[1-(5-{6-[6-(6-benzyloxycarbonyl-amino-hexanoylamino)-hexanoylamino]-hexanoylamino}-pentylcarbamoyl)-2S-phenyl-ethylcarbamoyl]-3(1S)-methyl-butylcarbamoyl}-2R-hydroxy-5-phenyl-pentyl)-carbamicacid tert-butyl ester Boc-Leu-Phe-OH was coupled with H$_2$N(CH$_2$)$_5$NH—LC—Z following General Procedure A. The resulting product was dissolved in ethanol and treated with 10% Pd/C and hydrogenated for 1 h at 50 psi. The reaction mixture was filtered through Celite and evaporated in vacuo. The resulting amine was coupled with HO—LC—LC—Z following General Procedure A and deprotected with TBAF following General Procedure D.

EXAMPLE 16 (SCHEME 7)

(4R-{1S-[1-(5-{6-[6-(6-Amino-hexanoylamino)-hexanoylamino]-hexanoylamino}-pentylcarbamoyl)-2-phenyl-ethylcarbamoyl]-3(1S)-methyl-butylcarbamoyl}-1S-benzyl-2R-hydroxy-5-phenyl-pentyl)-carbamic acid tert-butyl ester Boc-Leu-Phe-OH was coupled with H$_2$N(CH$_2$)$_5$NH—LC—Z following General Procedure A. The resulting product was dissolved in ethanol and treated with 10% Pd/C and hydrogenated for 1h at 50 psi. The reaction mixture was filtered through Celite and evaporated in vacuo. The resulting amine was coupled with HO—LC—LC-FMOC following General Procedure A, and the resulting product was deprotected with TFA following General Procedure C. The resulting amine was coupled with the product of Example 1 Step 2 (B) following General Procedure A and deprotected with TBAF following General Procedure D.

(1H, DMSO) 7.95–7.65 (6H, m), 7.27–7.02 (15H, m), 6.51 (1H, d, J=9), 4.75–4.70 (1H, m), 4.45–4.37 (1H, m), 4.25–4.05 (1H, m), 3.50–2.40 (22H, m), 1.60–1.05 (43H, m), 0.81 (3H, d, J=6.4), 0.75 (3H, d, J=6.4).

EXAMPLE 17

(1S,2R,4R,7S,10S)-[52-(hexahydro-2-oxo-1H-thieno[3,4-d]imidazol-4-yl)-2-hydroxy-7-(2-methylpropyl)-5,8,11,19,26,33,40,48-octaoxo-1,4,10-tris(phenylmethyl)-43,44-dithia-6,9,12,18,25,32,39,47-octaazadopentacont-1-yl] carbamic acid 1,1-dimethylester The product of Example 16 (5.48 mg) was reacted with sulfosuccinimidyl-2-(biotinamide)ethyl-1,3-dithiopropionate (NHS-SS-Biotin) (28 mg) in DMF. To this mixture was added 70 μL $H_2O$ and 30 μL of 20 mM sodium bicarbonate having pH 8.1. The reaction mixture was incubated at room temperature for 1 h. The temperature was increased to 70° C., and incubated for a further 1 h. The product was isolated using reverse phase HPLC. The peak eluting at 7.04 min was identified as the starting material and the peak at 19.53 min as the desired product. As confirmation the mass was identified as 1486.3.

For the avoidance of doubt the structures of Examples 1 to 16 can be found in the following schemes. In the case of ambiguity in the names given herein the structures below to be taken as correct.

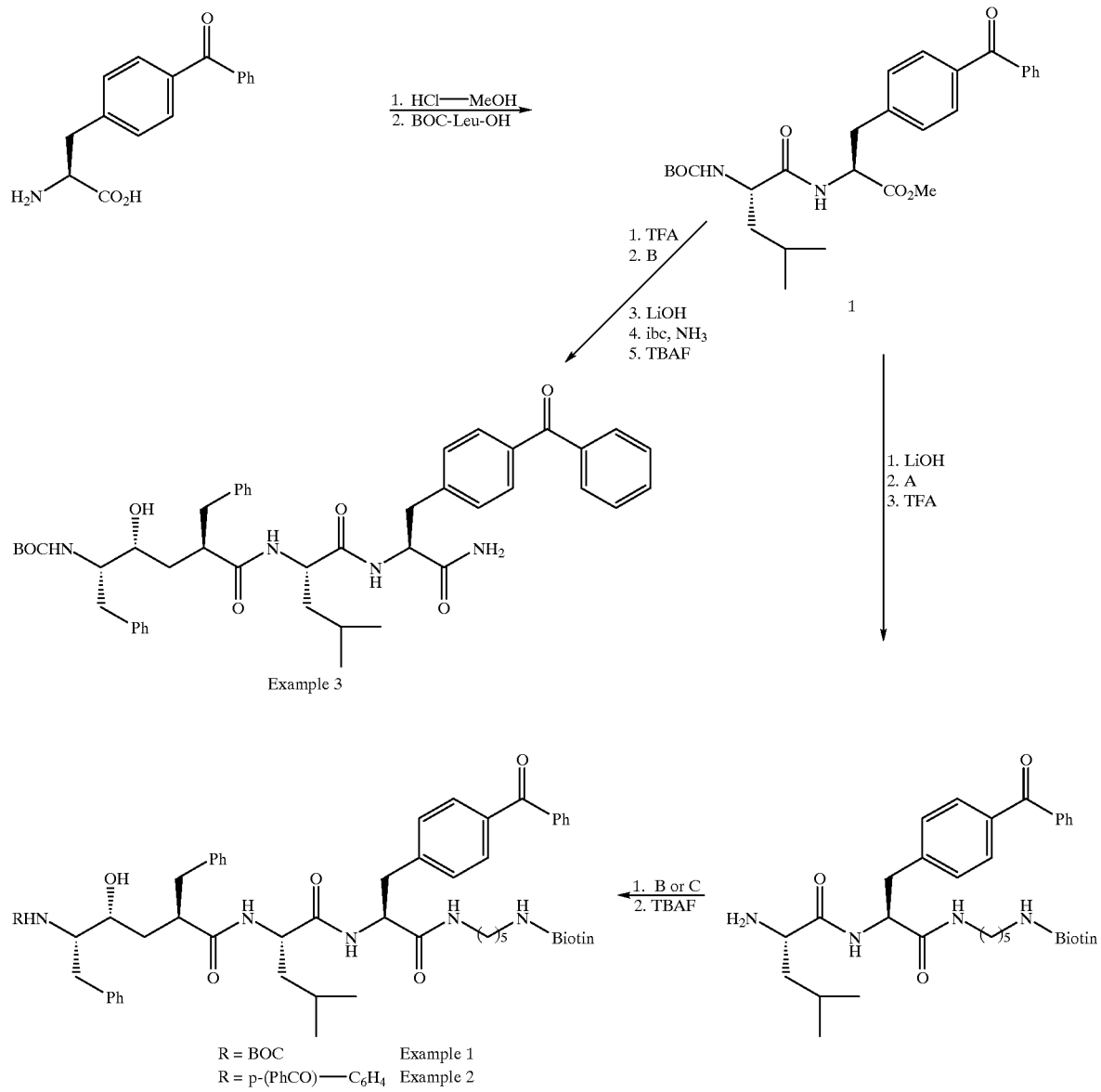

Scheme 1

Scheme 2
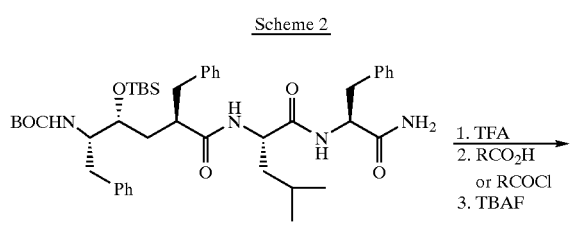
Example 5
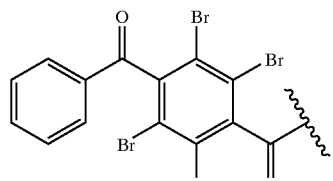
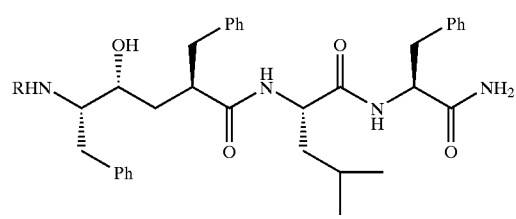
Example 6
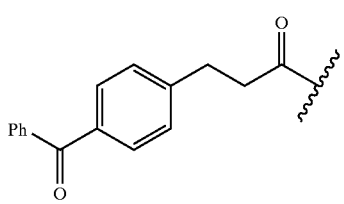
Example 4
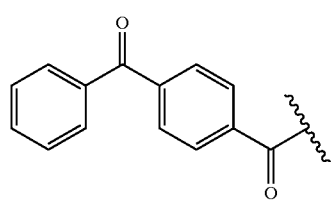
Example 7
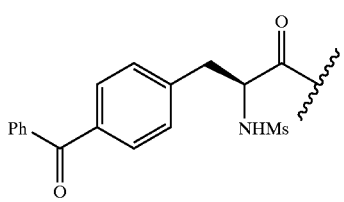
Scheme 3
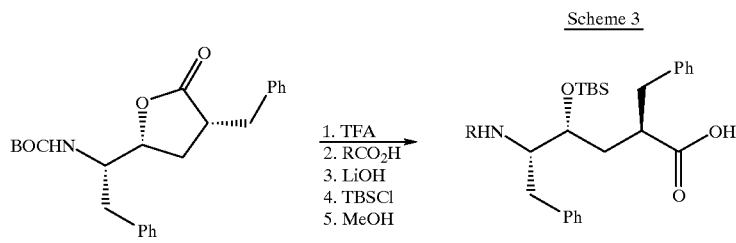
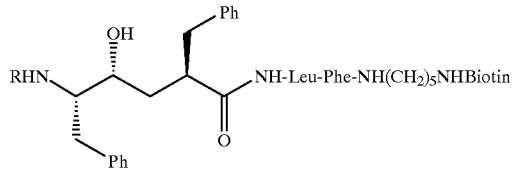
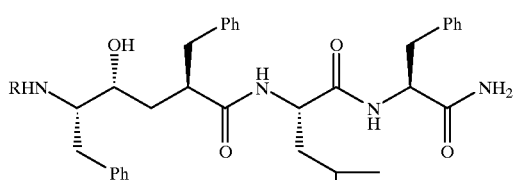
Example 9
Example 8
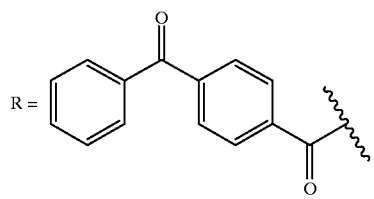
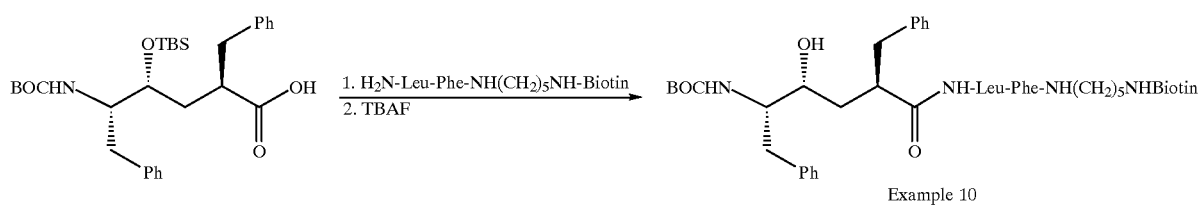
Example 10

Scheme 4
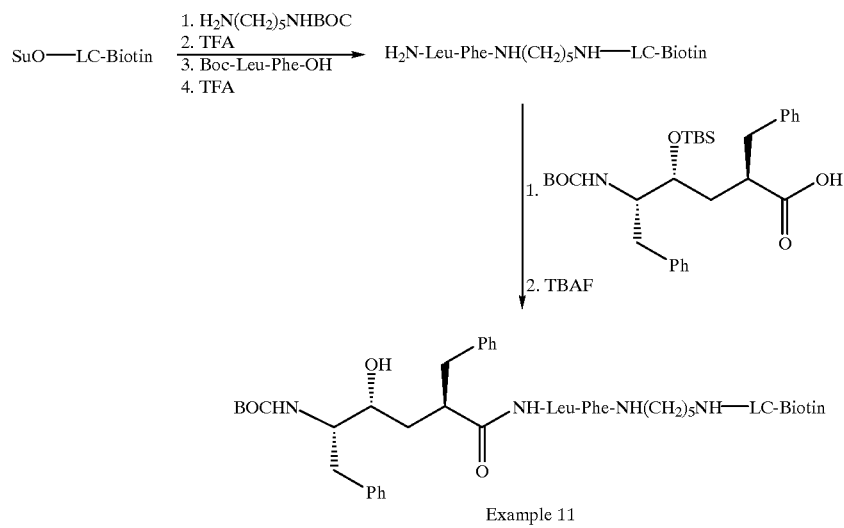
Example 11
Scheme 5
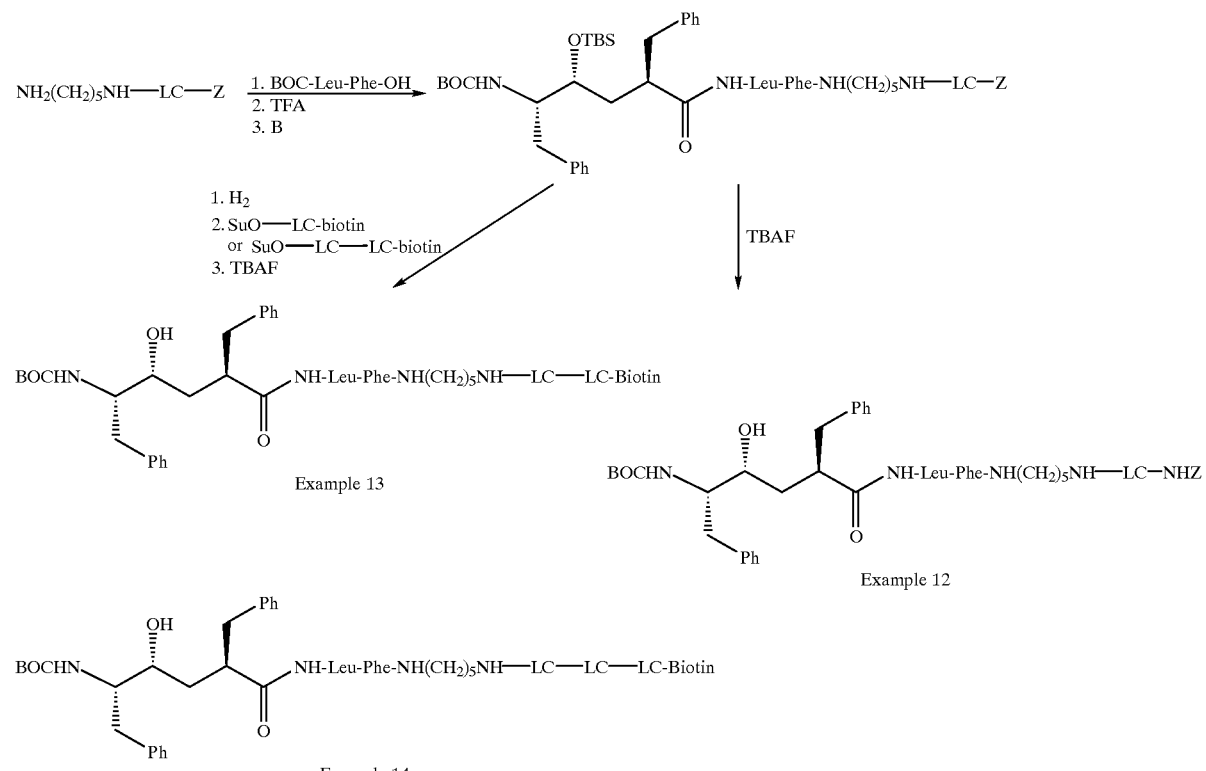
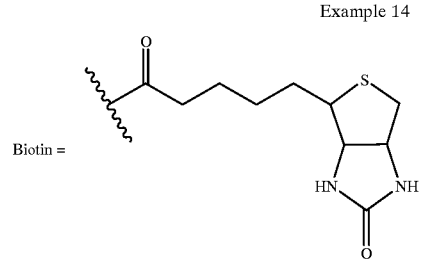

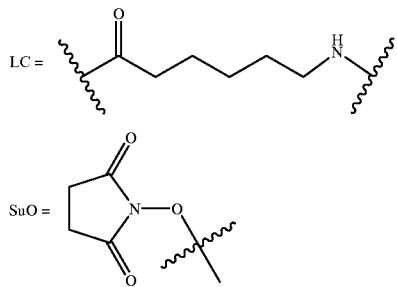

Scheme 6

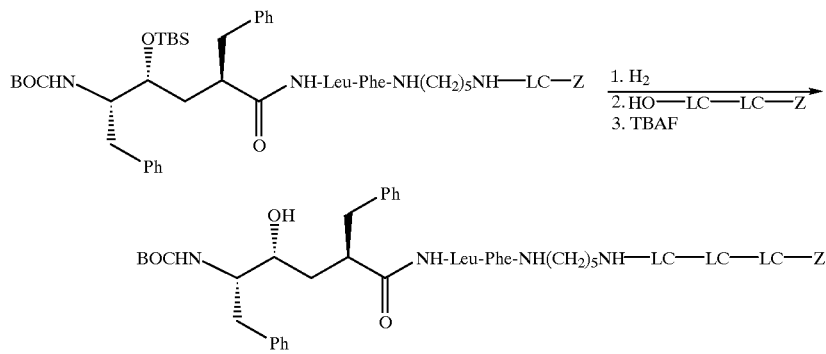

Example 15

Scheme 7

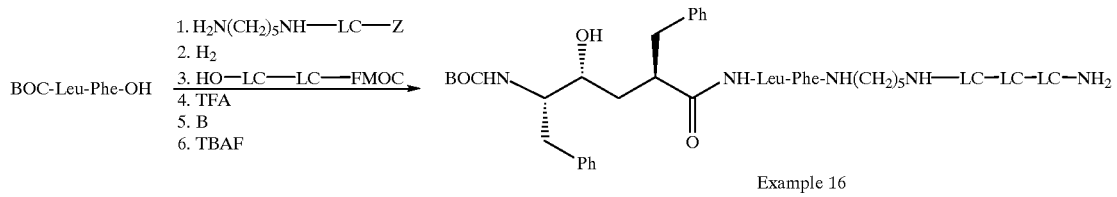

Example 16

What is claimed is:

1. A compound of formula I or a salt thereof:

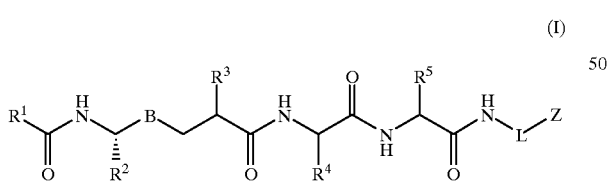

wherein:

R$^1$ is benzoylphenyl or benzoylphenylC$_{1-6}$alkyl wherein the benzoylphenyl moiety is optionally substituted by from one to nine bromine atoms and the alkyl moiety is optionally substituted by C$_{1-6}$alkylsulfonylamino; or C$_{1-6}$alkoxy;

R$^2$ and R$^3$ are independently chosen from C$_{1-10}$alkyl, C$_{1-10}$alkoxy, C$_{2-10}$alkenyl, C$_{2-10}$alkenyloxy, C$_{2-10}$alkynyl or C$_{2-10}$alkynyloxy; phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1,2 or 3 nitrogen atoms; and a group (CH$_2$)$_p$Q$^1$ wherein Q$^1$ is phenyl, naphthyl, a five-membered heteroaromatic ring containing 1, 2, 3 or 4 heteroatoms independently chosen from O, N and S, at most one of the heteroatoms being O or S, and a six-membered heteroaromatic ring containing 1, 2 or 3 nitrogen atoms; and wherein each of R$^2$ and R$^3$ is independently optionally substituted by one to three groups independently chosen from:

(a) halogen, cyano and nitro,
(b) hydroxy,
(c) C$_{1-3}$alkyl, C$_{2-3}$ alkenyl and C$_{2-3}$alkynyl,
(d) C$_{1-3}$alkoxy,
(e) NR$^6$R$^7$ wherein R$^6$ and R$^7$ are independently chosen from hydrogen, C$_{1-5}$alkyl and C$_{1-5}$alkoxyC$_{1-5}$alkyl,
(f) CO$_2$R$^8$ wherein R$^8$ is hydrogen or C$_{1-4}$alkyl,
(g) CONR$^6$R$^7$ or OCONR$^6$R$^7$ wherein R$^6$ and R$^7$ are independently as defined above,
(h) SO$_2$NR$^6$R$^7$ wherein R$^6$ and R$^7$ are independently as defined above,
(i) CH$_2$NR$^6$R$^7$ wherein R$^6$ and R$^7$ are independently as defined above, (j) N(R⁸)COR⁸' wherein R⁸ is independently as defined above and R⁸' is independently as defined for R⁸, (k) NR⁸SO₂R⁸' where R⁸ and R⁸' are independently as defined above;

alternatively R³ may be hydrogen;

R⁴ and R⁵ are independently chosen from hydrogen, $C_{1-6}$alkyl optionally substituted by halogen, hydroxy, thiol, amino, $C_{1-4}$alkoxy, $C_{1-4}$ alkylthio, carboxy, $C_{1-4}$ alkoxycarbonyl and $(CH_2)_q Q^2$ wherein $Q^2$ is a five-membered unsaturated heterocycle containing 1, 2, 3 or 4 heteroatoms optionally chosen from O, N, and S providing that not more than one heteroatom is O or S, a six-membered unsaturated heterocycle containing 1, 2 or 3 N atoms and phenyl and naphthyl, or a fused ring which is indolyl, each of the foregoing rings being optionally substituted with one to three groups independently chosen from hydroxy, $C_{1-4}$alkyl, $C_{1-4}$alkoxy, thiol, $C_{1-4}$alkylthio, halogen, amino, carboxy, amido, $CO_2H$ and —$NHC(NH_2)_2$ and wherein each of the foregoing rings is optionally fused to a benzene ring;

alternatively R⁵ may be benzoylbenzyl which is optionally substituted by from one to nine bromine atoms;

B is C=O or CHOH in the R configuration;

L is a bond or $[(CH_2)_m NHCO]_n$ in which one of the methylene groups may be replaced by a disulphide group;

Z is $(CH_2)_k$amino, benzoxy or biotin, or when L is a bond then Z is hydrogen, or biotin providing that when Z is hydrogen then either R¹ is not $C_{1-6}$alkoxy or R⁵ is benzoxybenzyl;

k is an integer of from one to ten;

each m is independently an integer of from one to ten;

n is an integer of from one to ten;

p is zero, one, two or three; and q is zero, one, two or three;

with the proviso that no carbon atom is substituted by more than one hydroxy group.

2. A compound of claim 1 of formula I':

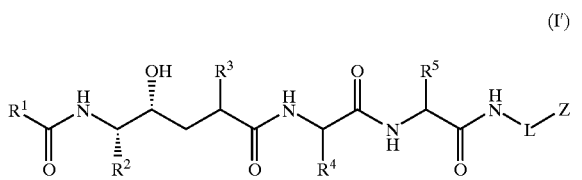

(I')

where R¹, R², R³, R⁴, R⁵, L and Z are as defined in claim 1.

3. A compound of claim 1 of formula I":

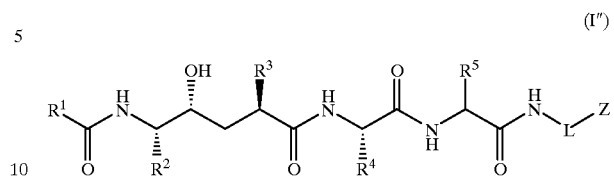

(I")

where R¹, R², R³, R⁴, R⁵, L and Z are as defined in claim 1.

4. A compound of claim 1 of formula I'":

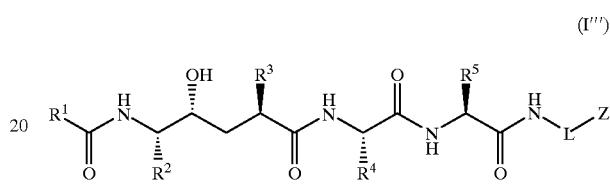

(I'")

where R¹, R², R³, R⁴, R⁵, L and Z are as defined in claim 1.

5. A compound according to claim 1 wherein:

R¹ is tertiarybutoxy, benzoylphenyl or benzoylphenyl$C_{1-2}$alkyl wherein the benzoylphenyl moiety is optionally substituted by from one to four bromine atoms and the $C_{1-2}$alkyl moiety is optionally substituted by methylsulfonylamino;

R² and R³ are benzyl;

R⁴ is isobutyl;

R⁵ is benzyl or benzoylbenzyl;

B is CHOH in the R configuration;

L is a bond or $[(CH_2)_m NHCO]_n$ in which one of the methylene groups may be replaced by a disulphide group;

Z is $(CH_2)_k$amino, benzoxy or biotin, or when L is a bond then Z is hydrogen providing either R¹ is not tertiary butoxy or R⁵ is not benzyl;

k is four;

m is five; and n is an integer of from one to five.

* * * * *